(12) United States Patent
Schlumpf

(10) Patent No.: US 7,637,876 B2
(45) Date of Patent: Dec. 29, 2009

(54) MULTIFUNCTIONAL CATHETER PROBE

(76) Inventor: Peter Schlumpf, Grabenackerstrasse 4, CH-8548 Ellikon an der Thur (CH)

( * ) Notice: Subject to any disclaimer, the term of this patent is extended or adjusted under 35 U.S.C. 154(b) by 735 days.

(21) Appl. No.: 11/239,637

(22) Filed: Sep. 29, 2005

(65) Prior Publication Data

US 2006/0079813 A1   Apr. 13, 2006

(30) Foreign Application Priority Data

Oct. 7, 2004   (CH) ..................... 1646/04

(51) Int. Cl.
*A61B 5/117* (2006.01)
*A61B 5/103* (2006.01)
(52) U.S. Cl. .................................... 600/587
(58) Field of Classification Search ................ 600/561, 600/593, 587, 528, 547, 549; 73/726, 781
See application file for complete search history.

(56) References Cited

U.S. PATENT DOCUMENTS 3,480,003 A * 11/1969 Crites .................. 600/593
4,776,347 A   10/1988 Matthews
4,809,710 A   3/1989 Williamson
5,427,114 A * 6/1995 Colliver et al. .............. 600/561
5,776,081 A   7/1998 Kreder
6,547,758 B1  4/2003 Rowland et al.
2001/0053920 A1  12/2001 Shaker
2003/0130679 A1  7/2003 Aliperti et al.

FOREIGN PATENT DOCUMENTS

EP   0 935 977   8/1999

* cited by examiner

*Primary Examiner*—Max Hindenburg
*Assistant Examiner*—Brian Szmal
(74) *Attorney, Agent, or Firm*—Pauley Petersen & Erickson

(57) ABSTRACT

A multifunctional catheter probe for carrying out intracorporal measurements, including a multiluminal flexible tubing divided into sections and joined together by coupling pieces and forming a multifunctional catheter probe. Each coupling piece has a central body with a central feed lumen leadthrough and measurement lumen lead-throughs which are arranged around. The coupling is accomplished with suitable attachment nipples to the lumens of the flexible tube sections. A measurement lumen passage closed in the passage has a radial opening in or on which different measuring devices for the manometric or electro-sensory are attached.

24 Claims, 3 Drawing Sheets

MULTIFUNCTIONAL CATHETER PROBE

BACKGROUND OF THE INVENTION

1. Field of the Invention

This invention relates to an element and to a multifunctional catheter probe for carrying out intracorporal measurements, in particular for the measurement of the closure force of a sphincter, according to the introductory parts of the independent patent claims.

2. Discussion of Related Art

Known catheters are used for measuring the closure force of sphincters, such as the esophageal sphincter, the sphincter oddi, the urethral sphincter and finally the anal sphincter. With this, the applied probes are different in their shaping, in particular in length and diameter, depending on the closure muscles to be measured.

With the use of electronic sensors in catheter probes, one may get measurements for the diagnosis in various regions. Typically, achalasias in the region of the esophagus, the urethra or the colon may be ascertained with intracorporal catheter probes, as well of course also pressure or pH-value readings in hollow organs, very generally.

Thus, it is particularly those measurements which, according to a manometric method, permit the measurement of the closure force of the sphincter, which are commonly applied. The measurement probes for manometric methods are usually disposable probes. The electronic measurement probes which may be used several times and which measure the closure force, in particular via piezoresistive measurement sensors, may in practice be used as often as possible, but are relatively expensive. With this form of probe, the pressure sensor is located in a balloon-like chamber which is filled with gel or a fluid to measure the produced pressure of the sphincter all around. This in principle however only leads to conclusions with regard to the pressure produced by the sphincter in its entirety, but not with regard to the locally occurring maximal pressure.

A further known device operates with a balloon catheter with which the closure force of the sphincter acts on the balloon and the closure force may be measured from this in a manometric manner. Such a solution requires no monitoring of the leakage which passes through the sphincter region, but the compressibility of the air is a problem. The temperature dependence can be an essential problem and also the total length of the measurement probe can be a problem.

The use of catheter probes for various applications with multiluminal flexible tubings has been known for years, such as taught by U.S. Patent Documents U.S. Pat. No. 6,547,758-B or US-2003/0130679-A.

Perfusion catheter probes for measuring the closure force of a sphincter are known from U.S. Patent Documents US-2001/0053920 and U.S. Pat. No. 4,809,710. Both catheter probes have peripheral measurement lumens which comprise measurement openings which are directed radially outwards and which are arranged distributed over the longitudinal direction of the probe between the proximal and the distal end. According to U.S. Patent Document U.S. Pat. No. 4,809,710, the measurement lumens are arranged about the central feed lumen in a helicoidal manner. In this manner, it becomes possible to arrange the measurement openings either distributed about the periphery or in the axial direction at the same angular position directly behind one another. The latter permits the anal sphincter to be examined over its entire length with regard to the closure force.

Balloon catheter probes for examining the closure force of the sphincter have been known for years, such as taught by U.S. Patent Documents U.S. Pat. No. 4,776,347, U.S. Pat. No. 5,776,081 and European Patent Document EP-A-0',935',977. Since with balloon catheters, practically only one centrically arranged lumen is provided in the catheter balloon for supplying water, and a second lumen for supplying pressurized air, usually here suitably considerably more simple, mostly only flexible tubings with two or three lumens are applied.

Also there are known measurement probes with which one or more radially outwardly directed openings are present on a flexible tubing, the openings being closed in each case by a membrane. The corresponding measurement lumens are filled with a fluid, and a pressure on the membrane leads to a pressure change in the corresponding lumen, so that it is possible to again measure the closure force of the sphincter in a manometric manner.

For the manufacturer of sphincter measurement probes, this means offering a large number of measurement probes of a different construction type and have a correspondingly large storage space, but despite this may practically not keep any complete manufactured probes in stock.

Added to this is the fact that the manufacture of measurement catheters of multiluminal flexible tubes with which lateral openings are incorporated at a later stage, and whose passages are closed by a suitable stopper, is complicated.

SUMMARY OF THE INVENTION

It is one object of this invention to provide a multifunctional catheter probe of the initially mentioned type, which permits all the previously mentioned types of measurement. This object is achieved with an element for such a probe as well as a multifunctional catheter probe using the element, as set forth in the specification and in the claims.

Further advantageous design forms of the subject-matter of this invention are also discussed in this specification and in the claims.

BRIEF DESCRIPTION OF THE DRAWINGS

The design and manner of operating of the subject-matter of this invention is explained in the subsequent description with reference to the accompanying drawings, wherein.

DESCRIPTION OF PREFERRED EMBODIMENTS

Figure 1:
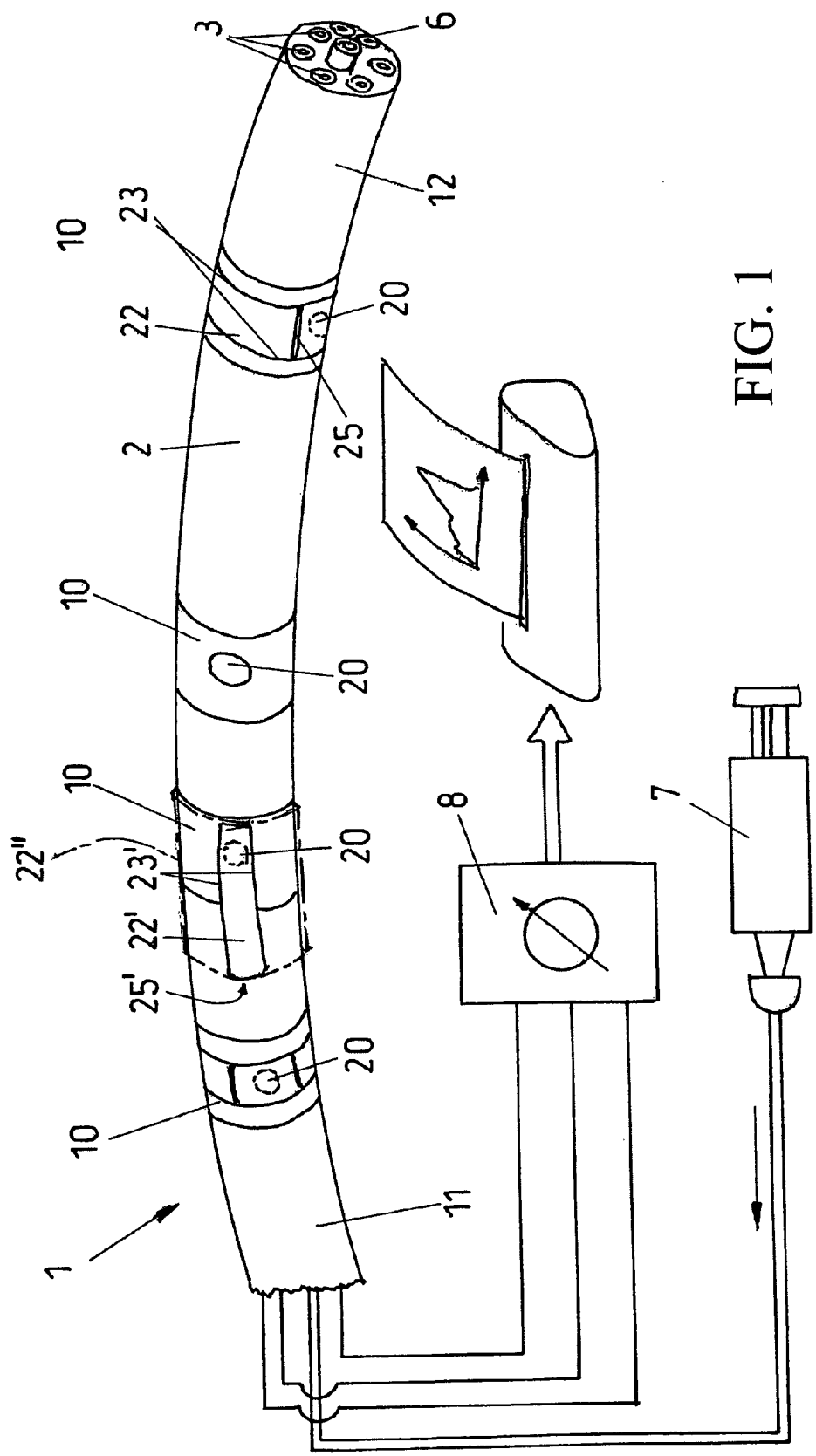
FIG. 1 is a perspective schematic view of a multifunctional catheter probe with several installed coupling pieces as probe elements.
Figure 3:
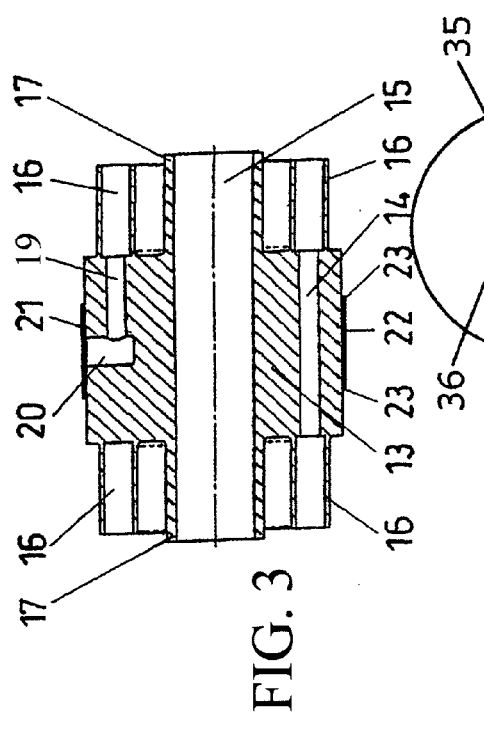
FIG. 3 shows a central vertical section taken through the coupling piece, along line A-A as shown in FIG. 2.

FIG. 1 shows a multifunctional catheter probe which is shown in its entirety as element 1, in a perspective representation, and schematically, the apparatus which may be peripherally connected. The multifunctional catheter probe 1 contains a multiluminal flexible tubing 2 which is divided at least into a proximal section 11 and a distal section 12. These two sections, as well as further sections are in turn connected to one another via a coupling piece 10. The multiluminal flexible tubing 2 comprises a number of peripheral measurement lumens 3 which are distributed about the periphery of a central feed lumen 6 at regular distances. There can be any suitable number of peripheral measurement lumens 3. Such multiluminal flexible tubings are available in various sizes and with a different number of peripheral measurement lumens. With regard to the form represented here, all peripheral measurement lumens run parallel to the central measurement lumen 6. Multiluminal flexible tubings with which the peripheral measurement lumens run around the central feed lumen in a helicoidal manner can be used if the coupling piece 10 is correspondingly adapted.

The multifunctional catheter probe according to this invention comprises at least two sections of the multiluminal flexible tubing 2 and at least one catheter probe element which for simplicity is referred to as a coupling piece 10. The multiluminal flexible tubing 2 is divided into as many sections as coupling pieces 10 which one wishes to add therebetween, depending on the number of different measurements to be taken. At the same time however the number of coupling pieces 10 which are to be added may not exceed the number of peripheral measurement lumens present in the multiluminal flexible tube 2. Thus, in the represented example, maximally eight coupling pieces may be applied between nine multiluminal flexible tubing sections. The various coupling pieces 10 thus neither need to be arranged at constant distances, nor do the individual coupling pieces 10 need to serve the same measurement method. Thus, in principle with regard to a multiluminal flexible tubing only may affect a complete separation anywhere where according to conventional methods, a radially outwardly directed opening is in one of the measurement lumens, and a coupling piece 10 according to this invention is inserted into this separation location. The manner of assembly is simple and quick.

The coupling piece 10 or the catheter probe element is preferably of one piece, for example is manufactured of plastic and has a central body 13 which is essentially cylindrical and whose diameter at least approximately corresponds to the diameter of the connecting multiluminal flexible tubing sections 11 and 12. The central body 12 is centrally passed through by a feed lumen lead-through 15. Measurement lumen lead-throughs 14 are arranged about the central passage 15 in an outwardly displaced and uniformly distributed manner. In each case, a measurement lumen attachment nipple 16 connects to each measurement lumen lead-through 14. The diameters of the measurement lumen attachment nipples 16 are adapted at least approximately to the inner diameter of the peripheral measurement lumen 3. In each case a feed lumen attachment nipple 17 is also integrally formed on both sides on the feed lumen lead-through 15. The outer diameter of this attachment nipple 17 corresponds at least approximately to the inner diameter of the central feed lumen 6. The arrangement of the attachment nipple 16 corresponds to the distribution of the measurement lumen in the multiluminal flexible tubing 2.

Although a measurement lumen lead-through does not completely pass through the central body 12, an attachment nipple 16 is present on both sides, because the attachment nipples 16 also serve for fastening multiluminal flexible tubing sections 11 and 12. As already mentioned, one measurement lumen passage 19 is closed on one side in the axial direction. This measurement lumen passage 19 roughly in the middle of the longitudinal extension of the central body 13 comprises an opening which is directed outwards in the radial direction. In order to keep the tooling costs as low as possible, in principle the radial opening 20 may be incorporated at a later stage by drilling. One advantage is that a significantly more expensive tool with a slide may be avoided. A suitable marking may be present on the outer surface of the central body 13 at the corresponding location at which the radial bore is incorporated.

One advantage of the catheter probe element 10 of this invention is that one may carry out all known manometric and electrical measurement methods with this simple coupling piece. In the simplest form one may simply leave open the radial opening 20 and one then has a perfusion catheter measurement probe which corresponds to the conventional system, with which in each case at one location, the multiluminal flexible tubing 2 with an opening is inserted in one of the measurement lumens. One no longer needs to insert a stopper into the measurement lumen as with conventional perfusion catheter measurement probes. The closure location is integrated in the coupling piece 10, according to this invention. The leading to the outside is then likewise effected in the coupling piece. Such an opening, in size and arrangement is very much more precise than an opening in one of the measurement lumens which is incorporated in the multiluminal flexible tubing at a later stage. With such an open arrangement one may measure a pointwise pressure in the sphincter region, wherein one either measures the pressure beyond which a leakage occurs and thus a pressure relief or no further pressure increase is possible, or a measurement is effected because the pressure is measured at the time in which a leakage is ascertained by way of a humidity or temperature sensor or a resistance measurement between two electrodes.

A further form of the pointwise measurement lies in sealingly bonding a membrane 26 over the radial opening 20. A predefined pressure remains in the correspondingly filled measurement lumen which communicates with that opening 20, which is covered by the measurement membrane 26. The pressure of the sphincter on the membrane may thus be measured in a manometric manner. This too corresponds to a known measurement method for which special measurement catheter probes are available on the market. A third embodiment is possible.

A means 21 for measuring the circumferential pressure runs at least approximately over the entire periphery of the central body 13. The means 21 in the simplest case may be a film strip 22 which is applied around the central body 13 and is connected to the central body 13 in a sealing manner at three sides. This sealing connection may be effected by bonding or by weld seams. The sealing is effected along at least approximately the entire length of the longitudinal edges 23 as well as on an end-edge 24. This end-edge connection must run as close as possible to the radially directed opening 20 and thus ensure that a measurement fluid run from the radially directed opening 20 practically completely around the central body 13 before this reaches the outside at the exit opening 25. A corresponding signal is measured according to the maximally occurring pointwise pressure over the entire periphery, which is effected by the sphincter. The measurement may be achieved by various known methods in which for example one carries out a throughput measurement by determining the manual pressure with which the measurement fluid begins to flow.

The means 21 may also be shaped in the form of a film flexible tubing 22", such as shown in FIG. 1, instead of the shape of a film strip 22. This film flexible tubing with its one opening is in communicating connection with the radially directed opening 20 and again be completely led around the central body 13 before the flexible tubing likewise ends in an exit opening. In this case, the flexible tube does not need to be bonded or welded along the longitudinal edges, but it must be secured on the central body 13 so that it cannot be displaced in the axial direction when the multifunctional catheter probe 1 is introduced.

Figure 7:
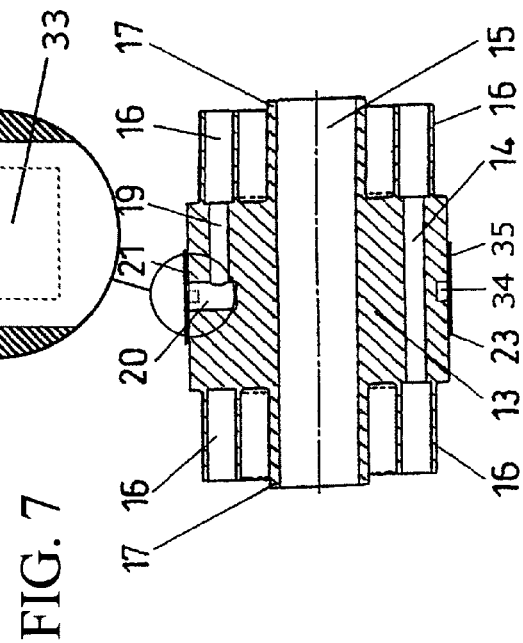
FIG. 7 shows a central vertical section as an alternative solution to the representation according to FIG. 3.
Figure 2:
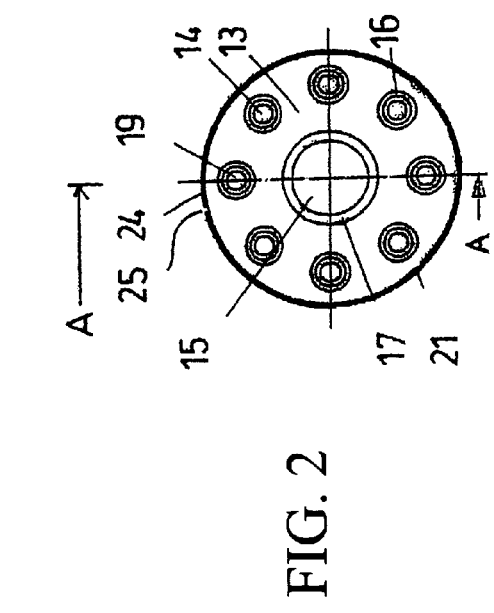
FIG. 2 shows a coupling piece in a view of a running direction of the lumens.
Figure 4:
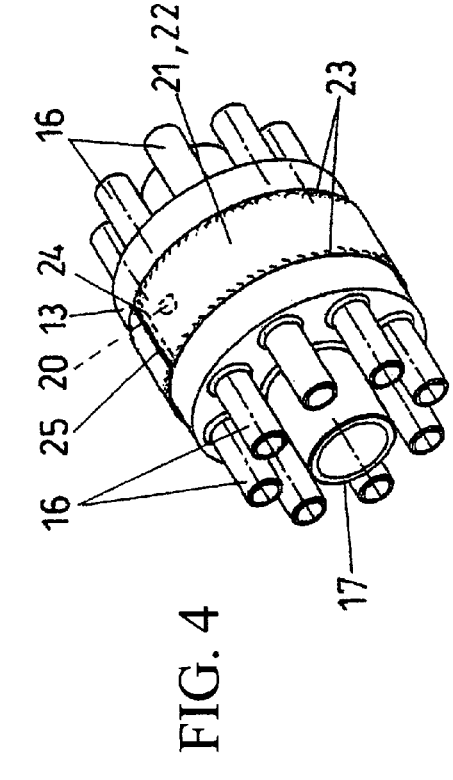
FIG. 4 shows a perspective view of a coupling piece according to this invention.

A further embodiment as shown in FIG. 7 may incorporate a peripheral annular groove 34 on the body at the central body of the coupling piece 10 from the opening 20 running in the radial direction, wherein the annular groove 34 ends at a remaining web 33 shortly before it runs again into the opening 20, so that again measurement fluid may be led practically around the entire central body 13. For this purpose, a shrinkage flexible tubing section 35 which closes this annular channel to the outside is applied over the central body 13. Then a suitable exit opening 25 in the form of a leakage opening 36 needs to be incorporated in the shrinkage flexible tubing shortly before the end of the annular channel close to the web 33. The leakage opening 36 may be affected in the shrinkage flexible tubing section 35 by perforation with a hot needle, preferably after a shrinking-on step.

In a further embodiment, a film strip 22∝ running approximately parallel to the flexible tubing axis is led over the central body 13 of the coupling piece 10 and over a part of an adjacent flexible tubing section. The film strip 22' is sealingly connected to the central body 13 or to the flexible tubing section at a narrow side close to the run-out of the radial measurement lumen opening 20 and along both longitudinal edges. Thus it forms a measurement flexible tubing section arranged in the longitudinal direction. Instead of a film strip, a film flexible tubing 22", similar to that shown in FIG. 1, running approximately parallel to the flexible tubing axis may be sealingly and integrally formed on the coupling piece 10 and on a part of the adjacent flexible tubing section, and is secured against displacement relative to the flexible tubing section and to the coupling piece 10, on this coupling piece.

A physician of conventional measurement methods knows all possible operating manners of the multifunctional catheter probe which may be carried out with the coupling piece 10 according to this invention.

As soon as the multifunctional catheter probe 1 is pushed forward far enough, then for example with a measurement of the sphincter of the urethra, the bladder may be filled with water or a solution via the central feed lumen in order to increase the bladder pressure to a desired level. The filling syringe 7 may for example be connected to the central feed lumen 6 via a Luer connection. The measurement lumens 3 are likewise connected via various Luer connections to a measurement station 8, by way of which a pressure prevailing in the measurement lumens may be measured. The data of the measurement station 8 may then be supplied to a PC with suitable software, for further processing, or may be printed out by a printer 9.

Figure 5:
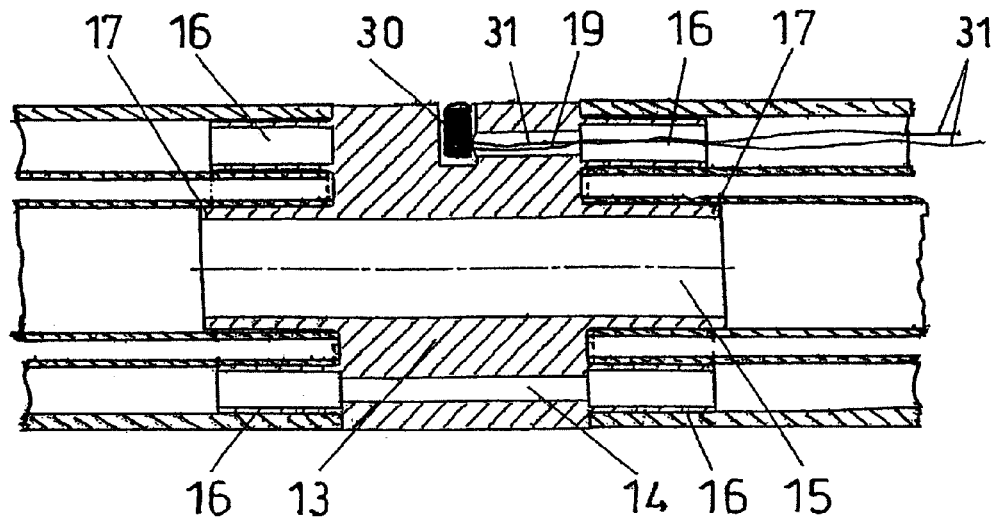
FIG. 5 shows an axial section taken through a coupling piece according to this invention, with an electronic sensor.
Figure 6:
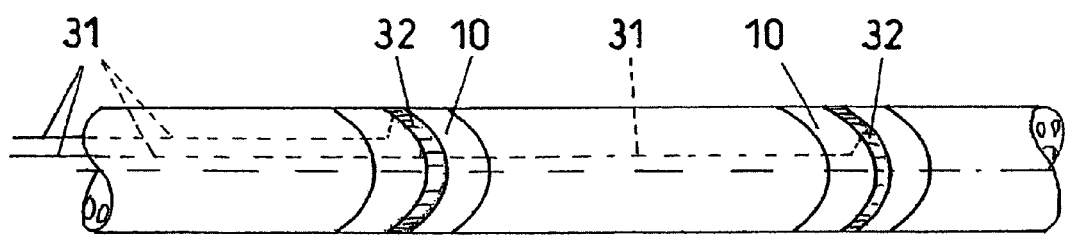
FIG. 6 shows a perspective schematic view of a catheter probe section with a coupling piece according to this invention, with a different electronic measurement probe.

As shown in FIG. 5, it is possible to use the radial opening 20 for attaching an electronic sensor 30. In this case, the measurement lumen passage 19 which is open at one side and which communicates with the radial opening 20, and the peripheral measurement lumen 3 connecting thereto may be used for leading through the electrical leads 31. The sensor can be of a silicon chip which converts a pressure acting on it into an electrical signal. This signal may be ascertained as a threshold value and thus effect a digital signal, or the measured value results in a proportional signal which may be used for an analogous evaluation.

The multifunctionality of the measurement probe element can also permit a metallic electrode ring 32 to be placed on the coupling piece 10, and the ring 32 in turn can have an electrical connection through the opening 20, the measurement lumen passage 10 and the peripheral lumen 3. If one attaches two rings onto two coupling elements distanced to one another, then with a change in resistance between the two rings one may ascertain a leakage detection in the urethra and create a so-called EMG (electromyogram).

Depending on whether the probe is formed with radial openings which are the same everywhere or with differently sealed or open radial openings, the physician then without having to change the catheter probe may perform all functions at various measurement locations which appear important. This saves time and material and burdens the patient significantly less to not need a catheter change.

Swiss Patent Reference 01646/04, the priority document corresponding to this invention, and its teachings are incorporated, by reference, into this specification.

What is claimed is:

1. A multifunctional catheter probe (1) for measurement of a closure force of a sphincter, comprising: a multiluminal flexible tubing (2) with a plurality of peripheral measurement lumens (3) arranged around a central feed lumen (6), the multiluminal flexible tubing (2) completely separated at least at one location, and the separated flexible tubing sections connected by an element (10) comprising a coupling piece for two sections of the flexible tubing and a central body (13) with lead throughs 14, 15) on which in an axial direction an attachment nipple (16, 17) is on both sides for each of the lumens (3, 6) of the multiluminal flexible tubing (2) for a sealed attachable connection of the lumens (3), at least one measurement lumen passage (19) within the central body (13) having a measurement lumen opening (20) led radially to an outside with the passage closed in the axial direction, a peripheral film strip (22) around the central body (13) of the coupling piece (10), and the film strip (22) at a narrow side near to a run out of the radial measurement lumen opening (20) and along both longitudinal edges (23) is sealingly connected to the central body (13) in a peripheral manner.

2. A multifunctional catheter probe (1) according to claim 1 wherein the element (10) is manufactured of plastic.

3. A multifunctional catheter probe (1) according to claim 1, wherein the film strip (22) is one of bonded and welded on the central body (13).

4. A multifunctional catheter probe (1) according to claim 1, wherein the coupling piece (10) has at least approximately the same diameter as the multiluminal flexible tubing (2).

5. A multifunctional catheter probe (1) according to claim 1, wherein at least one of the peripheral measurement lumens (3) is connected to a manometric measurement apparatus (8).

6. A multifunctional catheter probe (1) according to claim 1, wherein an electronic sensor (30) is arranged in the radial opening (14) of one of the coupling pieces (10) having electrical leads (31) led through the measurement lumen passage (19) open at one side, and through the connecting peripheral lumen (3) of the multiluminal flexible tubing (2) to a measurement station (8).

7. A multifunctional catheter probe (1) according to claim 1, wherein the sphincter is selected from the group consisting of an esophageal sphincter, a sphincter oddi, a urethral sphincter and an anal sphincter.

8. A multifunctional catheter probe (1) for measurement of a closure force of a sphincter, comprising: a multiluminal flexible tubing (2) with a plurality of peripheral measurement lumens (3) arranged around a central feed lumen (6), the multiluminal flexible tubing (2) completely separated at least at one location, and the separated flexible tubing sections connected by an element (10) comprising a coupling piece for two sections of the flexible tubing and a central body (13) with lead-throughs (14, 15) on which in an axial direction an attachment nipple (16, 17) is on both sides for each of the lumens (3, 6) of the multiluminal flexible tubing (2) for a sealed attachable connection of the lumens (3), at least one measurement lumen passage (19) within the central body (13) having a measurement lumen opening (20) led radially to an outside with the passage closed in the axial direction, a peripheral film flexible tubing is sealingly integrally formed on the measurement lumen opening (20), and the film flexible tubing is secured against axial displacement relative to the coupling piece (10) on the coupling piece.

9. A multifunctional catheter probe (1) according to claim 8, wherein the film flexible tubing is one of bonded and welded on the central body (13).

10. A multifunctional catheter probe (1) for measurement of a closure force of a sphincter, comprising: a multiluminal flexible tubing (2) with a plurality of peripheral measurement lumens (3) arranged around a central feed lumen (6), the multiluminal flexible tubing (2) completely separated at least at one location, and the separated flexible tubing sections connected by an element (10) comprising a coupling piece for two sections of the flexible tubing and a central body (13) with lead-throughs (14, 15) on which in an axial direction an attachment nipple (16, 17) is on both sides for each of the lumens (3, 6) of the multiluminal flexible tubing (2) for a sealed attachable connection of the lumens (3), at least one measurement lumen passage (19) within the central body (13) having a measurement lumen opening (20) led radially to an outside with the passage closed in the axial direction, the central body (13) surrounded by an annular groove (34) communicating with the measurement lumen opening (20), the groove forming a sealing web (33) arranged near the measurement lumen opening, a shrinkage flexible tubing section (35) closing off the annular groove attached over the central body (13), and the shrinkage flexible tubing section having a leakage opening (36) near the sealing web on a side distant to the radial measurement lumen opening (20).

11. A multifunctional catheter probe (1) for measurement of a closure force of a sphincter, comprising: a multiluminal flexible tubing (2) with a plurality of peripheral measurement lumens (3) arranged around a central feed lumen (6), the multiluminal flexible tubing (2) completely separated at least at one location, and the separated flexible tubing sections connected by an element (10) comprising a coupling piece for two sections of the flexible tubing and a central body (13) with lead-throughs (14, 15) on which in an axial direction an attachment nipple (16, 17) is on both sides for each of the lumens (3, 6) of the multiluminal flexible tubing (2) for a sealed attachable connection of the lumens (3), at least one measurement lumen passage (19) within the central body (13) having a measurement lumen opening (20) led radially to an outside with the passage closed in the axial direction, and the measurement lumen opening (20) is sealingly closed with a membrane (30).

12. A multifunctional catheter probe (1) for measurement of a closure force of a sphincter, comprising: a multiluminal flexible tubing (2) with a plurality of peripheral measurement lumens (3) arranged around a central feed lumen (6), the multiluminal flexible tubing (2) completely separated at least at one location, and the separated flexible tubing sections connected by an element (10) comprising a coupling piece for two sections of the flexible tubing and a central body (13) with lead throughs (14, 15) on which in an axial direction an attachment nipple (16, 17) is on both sides for each of the lumens (3, 6) of the multiluminal flexible tubing (2) for a sealed attachable connection of the lumens (3), at least one measurement lumen passage (19) within the central body (13) having a measurement lumen opening (20) led radially to an outside with the passage closed in the axial direction, a film strip (22') running approximately parallel to the flexible tubing axis led over the central body (13) of the coupling piece (10) and over a part of an adjacent flexible tubing section, the film strip (22') on a narrow side near to a run in of the measurement lumen opening (20) and along both longitudinal edges (23') sealingly connected to one of the central body (13) and the flexible tubing section, and forms a measurement flexible tubing section arranged in the longitudinal direction.

13. A multifunctional catheter probe (1) according to claim 12, wherein the film strip (22') is one of bonded and welded on the central body (13) and on the flexible tubing section.

14. A multi functional catheter probe (1) for measurement of a closure force of a sphincter, comprising: a multiluminal flexible tubing (2) with a plurality of peripheral measurement lumens (3) arranged around a central feed lumen (6), the multiluminal flexible tubing (2) completely separated at least at one location, and the separated flexible tubing sections connected by an element (10) comprising a coupling piece for two sections of the flexible tubing and a central body (13) with lead-throughs (14, 15) on which in an axial direction an attachment nipple (16, 17) is on both sides for each of the lumens (3, 6) of the multiluminal flexible tubing (2) for a sealed attachable connection of the lumens (3), at least one measurement lumen passage (19) within the central body (13) having a measurement lumen opening (20) led radially to an outside with the passage closed in the axial direction, a film flexible tubing running approximately parallel to the flexible tubing axis sealingly integrally formed on the measurement lumen opening (20) over the central body (13) of the coupling piece (10) and over a part of an adjacent flexible tubing section, and secured against displacement relative to the flexible tubing section and to and on the coupling piece (10).

15. A multifunctional catheter probe (1) according to claim 14, wherein the film flexible tubing is one of bonded and welded on the central body (13) and on the flexible tubing section.

16. A multifunctional catheter probe (1) according to claim 15, wherein the coupling piece (10) has at least approximately the same diameter as the multiluminal flexible tubing (2).

17. A multifunctional catheter probe (1) according to claim 16, wherein a plurality of coupling pieces (10) are arranged at different angular positions relative to one another in the multiluminal flexible tubing (2).

18. A multifunctional catheter probe (1) according to claim 17, wherein coupling pieces (1) for measurement according to different methods are arranged in a multiluminal flexible tubing (2) divided into several sections.

19. A multifunctional catheter probe (1) according to claim 18, wherein at least one of the peripheral measurement lumens (3) is connected to a manometric measurement apparatus (8).

20. A multifunctional catheter probe (1) according to claim 17, wherein an electronic sensor (30) is arranged in the radial opening (14) of one of the coupling pieces (10) having electrical leads (31) led through the measurement lumen passage (19) open at one side, and through the connecting peripheral lumen (3) of the multiluminal flexible tubing (2) to a measurement station (8).

21. A multifunctional catheter probe (1) according to claim 17, wherein a metallic electrode ring (32) is arranged over two distanced coupling elements (10), and the connected electrical leads (31) are led through the corresponding radial openings (14) and the connecting measurement lumen (19) open at one side, and the through peripheral measurement lumen (3) of the flexible tube, to a measurement station (8).

22. A multifunctional catheter probe (1) according to claim 19, wherein the sphincter is selected from the group consisting of an esophageal sphincter, a sphincter oddi, a urethral sphincter and an anal sphincter.

23. A multifunctional catheter probe (1) for measurement of a closure force of a sphincter, comprising: a multiluminal flexible tubing (2) with a plurality of peripheral measurement lumens (3) arranged around a central feed lumen (6), the multiluminal flexible tubing (2) completely separated at least at one location, and the separated flexible tubing sections connected by an element (10) comprising a coupling piece for two sections of the flexible tubing and a central body (13) with lead-throughs (14, 15) on which in an axial direction an attachment nipple (16, 17) is on both sides for each of the lumens (3, 6) of the multiluminal flexible tubing (2) for a sealed attachable connection of the lumens (3), at least one measurement lumen passage (19) within the central body (13) having a measurement lumen opening (20) led radially to an outside with the passage closed in the axial direction, and a plurality of coupling pieces (10) arranged at different angular positions relative to one another in the multiluminal flexible tubing (2).

24. A multifunctional catheter probe (1) for measurement of a closure force of a sphincter, comprising: a multiluminal flexible tubing (2) with a plurality of peripheral measurement lumens (3) arranged around a central feed lumen (6), the multiluminal flexible tubing (2) completely separated at least at one location, and the separated flexible tubing sections connected by an element (10) comprising a coupling piece for two sections of the flexible tubing and a central body (13) with lead-throughs (14, 15) on which in an axial direction an attachment nipple (16, 17) is on both sides for each of the lumens (3, 6) of the multiluminal flexible tubing (2) for a sealed attachable connection of the lumens (3), at least one measurement lumen passage (19) within the central body (13) having a measurement lumen opening (20) led radially to an outside with the passage closed in the axial direction, and coupling pieces (1) for measurement according to different methods arranged in a multiluminal flexible tubing (2) divided into several sections.

* * * * *